United States Patent [19]

Harrison et al.

[11] Patent Number: 4,562,272

[45] Date of Patent: Dec. 31, 1985

[54] PROCESS FOR PREPARING CYCLIC POLYETHERS

[75] Inventors: Arnold M. Harrison, South Charleston; Leonard Kaplan, Dunbar, both of W. Va.

[73] Assignee: Union Carbide Corporation, Danbury, Conn.

[21] Appl. No.: 248,268

[22] Filed: Mar. 27, 1981

[51] Int. Cl.$^4$ .............................................. C07D 323/00
[52] U.S. Cl. ....................................... 549/352; 549/353
[58] Field of Search ................... 260/338; 549/352, 353

[56] References Cited

U.S. PATENT DOCUMENTS 3,928,386  12/1975  Dale et al. ............................ 260/338
3,997,563  12/1976  Dale et al. ............................ 260/338

FOREIGN PATENT DOCUMENTS 785229  10/1957  United Kingdom .

OTHER PUBLICATIONS

Charles J. Pedersen, *J. Amer. Soc.*, 89, 2495–2496, (1967).
R. F. Golden in "Glycols", Edited by George O. Curme, Jr., p. 277, American Chemical Society Monograph, Reinhold, New York, 1952.
J. L. Down, J. Lewis, B. Moore and G. Wilkinson, *J. Chem. Soc.*, 3767–3773, (1959).
R. J. Kern, *J. Org. Chem.*, 33 (1), 388–390, (1968).
Johannes Dale, Gerd Borgen and Kari Dassvatn, *Acta Chem. Scand. B.*, 28 (3), 378–379, (1974).
Johannes Dale and Kari Dassvatn, *J.C.S. Chem., Comm.*, 295–296, (1976).
Johannes Dale, Kari Dassvatn and Jrules Gronneberg, *Makromol, Chem.*, 178, 873–879, (1977).
E. J. Goethans, *Pure & Appl. Chem.*, 48,335, (1976).
Yuhsuke Kawakami and Yuga Yamashita, *Macromolecules*, 10(4), 837–840, (1977).
Warner W. Carlson and Leonard H. Cretcher, *J. Amer. Chem. Soc.* 69, 1952–1956, (1947).
Jeruo Yoshino, Shigeru Inaba, Hajime Komura and Yoshiharu Ishido, *Bull. Chem. Soc. Japan*, 47(2), 405–409, (1974).
Yoshiharu Ishido, Hideo Jsutsumi and Shigeru Inaba, *J.C.S. Perkin I,* 521–530, (1977).
A. L. Shapiro, I. S. Lyubovskii, V. I. Romanova and S. Z. Levin, *J. Org. Chem. of U.S.S.R.*, (English transl.), 6 (7), 1380–1383, (1970).
A. L. Shapiro, S. Z. Levin and V. P. Chekhovskaya, *J. Org. Chem. of U.S.S.R.*, (Eng. transl.) 5 (2), 200–203, (1969).
A. L. Shapiro, S. Z. Levin and V. P. Chekhovskaya, *J. Org. Chem. of U.S.S.R.*, (Eng. transl.), 4 (12), 1995–1998, (1968).
J. M. McKenna et al., Macromolecules, vol. 10(4), (1977), pp. 877–879.

*Primary Examiner*—Norma S. Milestone
*Attorney, Agent, or Firm*—Norman L. Balmer

[57]          ABSTRACT

The invention relates to a process for preparing cyclic polyethers from cyclic alkylene carbonates in the presence of a solvent, wherein the process is carried out in the presence of a solvent selected from the group containing a carbonyl moiety, nitrile moiety or mixture thereof. In addition, ionic catalysts may be employed to increase the selectivity to cyclic polyether.

16 Claims, No Drawings

PROCESS FOR PREPARING CYCLIC POLYETHERS

FIELD OF THE INVENTION

This invention relates to a new and valuable process for preparing cyclic polyethers of the general formula:

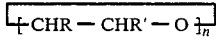

wherein R and R' are selected from the group consisting of hydrogen, alkyl, aryl, araalkyl, asnd alkylaryl, and n is an integer having a value of at least 3.

BACKGROUND OF THE INVENTION

Extensive work over the past years has demonstrated the immense value and novel chemical nature of cyclic polyethers. For example, see "Synthetic Multidentate Macrocyclic Compounds", edited by Reed M. Izatt and James J. Christensen, Academic Press, New York (1978) and "Progress in Macrocyclic Chemistry, Volume 1", edited by Reed M. Izatt and James J. Christensen, John Wiley and Sons, New York, (1979), for ample description of the structures and nomenclature related to these cyclic polyethers.

As recently as 1978 J. S. Bradshaw [in "Synthetic Multidentate Macrocyclic Compounds," ed. R. M. Izatt and J. J. Christensen, Academic Press, 1978, p. 53] referred to "the so-called crown class of compounds first prepared by Pedersen (1967)." On p. 10 of the same book C. J. Pedersen stated:

> Only a few publications prior to 1967 referred to polyethers, and none of them considered the possibility of their forming complexes with the salts of the alkali and alkaline earth metals. Of the previously reported compounds, the most closely related to the crown compounds were 2,2,7,7,12,12,17,17-octamethyl-21,22,23,24-tetraoxaquatrene, $C_{28}H_{32}O_4$, made by condensing acetone with furan (Ackman et al., 1955); 2,3,12,13,22,23-tribenzo-1,4,11,14,21,24-hexaoxacyclotriaconta-2,12,22-triene (tribenzo-30-crown-6), $C_{36}H_{48}O_6$, and 2,3,12,13-dibenzo-1,4,11,14-tetraoxacycloeicosa-2,12-diene (dibenzo-20-crown-4), $C_{24}H_{32}O_4$ (FIG. 4, XIX) (Luttringhaus and Sichert-Modrow, 1956). Cyclic tetramers of ethylene oxide (Stewart et al., 1957) and propylene oxide (Down et al., 1957, 1959) had also been synthesized previously.

However, see also: A. Luttringhaus and K. Ziegler, Ann., 528, 155 (1937); A. Luttringhaus, Ann., 528, 181, 211, 233 (1937); R. Adams and L. N. Whitehill, J. Am. Chem. Soc., 63, 2073 (1941); W. J. Toussaint and D. R. Jackson, unpublished work, 1945, reported by R. F. Holden, in "Glycols," ed. G. O. Curme, Jr., and F. Johnston, A.C.S. Monograph Series, 1952, p. 274; J. B. Rose, J. Chem. Soc., 542, 546 (1956); J. L. Down, J. Lewis, B. Moore, and G. Wilkinson, Proc. Chem. Soc., 209 (1957); J. L. Down, J. Lewis, B. Moore, and G. Wilkinson, J. Chem. Soc., 3767 (1959); R. O. Colclough and K. Wilkinson, J. Polymer Sci. (C), No. 4, 311 (1963). Note especially the report of pentamethyl-15-crown-5 and hexamethyl-18-crown-6 by Holden and the comment by Down, Lewis, Moore, and Wilkinson that "the chelating possibility of this ether [tetramethyl-12-crown-4] is obviously important."

J. S. Bradshaw and P. E. Stott, Tetrahedron, 36, 461 (1980) have summarized work on procedures which are variatons of the Williamson ether synthesis.

Additional, recent, reports include: M. Okahara, M. Miki, S. Yanagida, I. Ikeda, and K. Matsushima, Synthesis, 854 (1977); R. O. Trucks and E. C. Steiner, U.S. Pat. No. 4,113,739 (1978); M. Okahara, I. Ikeda, and S. Yanagida, Japan Patent Publications 98985 (1978) and 119483 (1979); L. Mandolini and B. Masci, Synth. Comm., 9, 851 (1979); N. Kawamura, M. Miki, I. Ikeda, and M. Okahara, Tet. Lett., 535 (1979); P.-L. Kuo, N. Kawamura, M. Miki, and M. Okahara, Bull. Chem. Soc. Japan, 53, 1968 (1980); I. Ikeda, S. Yamamura, Y. Nakatsuji, and M. Okahara, J. Org. Chem., 45, 5355 (1980); B. Czech, Tet. Lett., 4197 (1080). Bradshaw and Stott also discuss an alternate method based on direct acid catalyzed oligomerization of ethylene oxide using a cationic template.

However, it is obvious that only a direct process from the cheap petrochemical raw material ethylene oxide can make possible the large scale industrial preparation of these valuable cyclic ethers.

In applicants co-pending U.S. Ser. No. 248,532, filed Mar. 22, 1981, a process is disclosed for preparing cyclic polyethers from alkylene oxides in the presence of a catalyst selected from the group consisting of alkali halides, alkaline earth halides and mixtures thereof.

The use of ethylene carbonate as an ethoxylating agent has been reported in the literature; see W. W. Carlson and L. H. Crelcher, J. Amer. Chem. Soc., 69, 1952 (1947) and T. Yoshino, S. Inaba, H. Komura, and Y. Ishido, Bull. Chem. Soc. Japan, 47 (2), 405 (1974).

The decomposition of ethylene carbonate in the presence of alkali halides is disclosed in an article by Y. Ishido, H. Tsutsumi, and S. Inaba, J. C. S. Perkin I, 521 (1977) and by A. L. Shapiro, S. Z. Levin, and V. P. Chekhovskaya, Zh. Org. Chem of U.S.S.R., 5 (2), 207 (1969). In addition the article by Shapiro et al., discloses that the alkali metal halides decompose ethylene carbonate to form ethylene oxide and carbon dioxide. The formation of polyethylene oxide is disclosed as the only product formed when lithium, sodium, or potassium fluoride are employed. The use of chlorides of lithium, sodium, potassium, and cesium and the bromides and iodides of lithium, sodium and potassium is disclosed to give ethylene oxide and polyethylene oxide when employed at 200° C. (see Table I on page 201 thereof). Other reports of the reaction of cyclic alkylene carbonates with halide salts include E. D. Bergmann and F. Shahak, J. Chem. Soc. (C), 899 (1966); Y. Wu, U.S. Pat. No. 4,111,965 (1978); T. Yoshino, S. Inaba, and Y. Ishido, Bull. Chem. Soc. Japan, 46, 553 (1973); T. Yoshino, S. Inabe, H. Komura, and Y. Ishido, JCS Perkin 1, 1266 (1977); A. Hilt, J. Trivedi, and K. Hamann, Makromol. Chem., 89, 177 (1965); E. Schwenk, K. Gulbins, M. Roth, G. Benzing, R. Maysenholder, and K. Hamman, Makromol. Chem., 51, 53 (1962); A. M. Ryzhenkov, A. L. Shapiro, V. S. Mozhenko, in Alkilenkarbonaty, ed. V. V. Shipikin, Leningrad, 1975, p. 87; A. L. Shapiro, V. P. Chekhovskaya and B. L. Vorob'ev, ibid., p. 94; A. L. Shapiro, I. S. Lyubovskii, V. P. Chekhovskaya and B. L. Vorob'ev, ibid p. 103; S. Sarel, T. Rand-Meir, and A. Poles, Israel J. Chem., 2, 237 (1964); K. Gulbins, G. Benzing, R. Maysenholder, and K. Hamann, Chem. Ber., 93, 1975 (1960); D. Grobelny, P.Maslak, and S. Witek, Tet. Lett., 2639 (1979); A. Lemaire, K. J. Schroader, and M. F. Reed, J. Labelled Compd. Radiopharm., 13, 211 (1977) [Chem. Abstr. 87, 52682q (1977)]. None of these publications reports the formation of a cyclic polyether in these reactions.

SUMMARY OF THE INVENTION

In accordance with the teachings of the invention, a process is provided for the formation of cyclic polyethers from cyclic alkylene carbonates. It has been discovered that such cyclic polyethers may be formed from cyclic alkylene carbonates in the presence of a solvent which contains a carbonyl moiety or nitrile moiety such that cyclic polyether is formed. Ionic salt catalysts may also be employed in admixture witth said cyclic alkylene carbonate and solvent.

DETAILED DESCRIPTION OF THE INVENTION

According to the invention there is provided a process for preparing cyclic polyethers, including substituted polyethers, by providing in admixture a cyclic alkylene carbonate, solvent and, optionally, an ionic salt.

The cyclic alkylene carbonates with which the present process may be practiced are those carbonates that are polymerizable cyclic carbonates of the general formula:

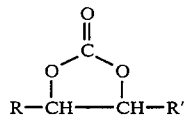

wherein R and R' are selected from the group consisting of hydrogen, alkyl, arykl, araalkyl, and alkylaryl. R and R' are generally selected from the group consisting of hydrogen or alkyl, both straight chain and branched, having from 1 to 20 carbon atoms, preferably from 1 to 10 carbon atoms. Thus, the cyclic alkylene carbonates used herein include both substituted and unsubstituted cyclic alkylene carbonates, including but not limited to, ethylene carbonate, 1,2-propylene carbonate, 1,2- and 2,3-butylene carbonate, 1,2-octene carbonate, styrene carbonate, and the like. The preferred cyclic alkylene carbonates are the vicinal alkylene carbonates with the most preferred being ethylene carbonate.

The choice of solvents is such that the solvent contains a carbonyl moiety,

a nitrile moiety (—C≡N) or mixtures thereof such that when employed in the process of this invention the aforementioned cyclic polyethers are formed. Exemplary solvents suitable for the process include, but are not limited to, acetone, 2,4-pentanedione, dimedone, mesityl oxide, 2-butanone, 2-pentanone, 3-pentanone, 1,3-diphenyl-2-propanone, 1,1-diphenyl-2-propanone, butyrolactone, benzyl cyanide, diphenylacetonitrile, n-butyronitrile, isophorone, diethylmalonate dimethylmalonate, 2-octanone, 2-hexanone, 2-heptanone, cycloheptanone, 2-decanone, acetonitrile and the like. In addition, the solvent must not be consumed by the process or side reactions related thereto. Not all the carbonyl- and nitrile-containing solvents necessarily function effectively in all embodiments of the process of this invention. In some cases a given selected solvent for a particular selected cyclic alkylene carbonate may not function effectively and some degree of selection between the solvent, cyclic alkylene carbonate, the reaction parameters, and, optionally, the ionic catalyst may be required to obtain cyclic polyethers.

The solvent is generally employed in an amount such that the ratio, by weight, to cyclic alkylene carbonate is from about 5:95 to about 95:5, preferably from about 1:10 to about 10:1 and most preferably from about 1:4 to about 4:1.

The ionic catalysts which may be employed in admixture with the cyclic alkylene carbonate and solvent include any ionic salt and preferably those ionic salts that do not destroy the solvent or the products, e.g., the cyclic polyether. The ionic catalyst is generally a salt of a Group IA, IIA, IB or IIB metal or mixtures thereof, more preferably a halide of the Group IA metals and mixtures thereof, and most preferably the halides of potassium, rubidium or cesium and mixtures thereof. The concentration of ionic catalyst may vary depending on the cyclic alkylene carbonate and solvent selected but is generally in the range of from 0.01 to about 10 molar and is preferably in the range of from about 0.01 to about 1.0 molar. In addition, it is believed that solid catalyst with saturated solutions may be employed.

The temperature at which the process is practiced is not narrowly critical. The process temperature is typically from about 100° C. to about 300° C. and is preferably from about 150° C. to about 225° C.

The process may be carried out at subatmospheric, atmospheric, or superatmospheric pressures. Atmospheric (14.7 psia) and superatmospheric pressures are believed to be preferred.

The cyclic polyethers formed according to the process of this invention are those of the general formula:

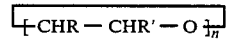

wherein R and R' are selected from the group consisting of hydrogen, alkyl, aryl, araalkyl, and alkylaryl and n is an integer having a value of at least 3, preferably from 3 to 11. R and R' are preferably selected from the group consisting of hydrogen and alkyl, said alkyl having from 1 to 20 carbon atoms, preferably from 1 to 10 carbon atoms. Included in this class of cyclic polyethers are 15-Crown-5 and 18-Crown-6.

EXPERIMENTAL PROCEDURE

The following examples were carried out by introducing about 1 milliliter of a solution of ethylene carbonate with or without other solvent into a glass NMR tube (7 inch × 5 mm). If an ionic catalyst was employed, 1 mmole of said catalyst, unless otherwise indicated, was placed in the NMR tube prior to addition of the solution into the NMR tube. The NMR tubes were prepared in a nitrogen glove box. The tubes were then stoppered, removed from the glove box, cooled in dry ice and sealed with a nitrogen or argon atmosphere in the free space at the top of each tube. Each tube was then placed in a stainless steel mini bomb (⅜ inch stainless steel tube with pressure fittings on each end and glass wool padding at each end). Dry ice was added to the free space in each mini-bomb.

The mini-bombs (one or more) were placed in a 3 liter rocker bomb and the entire bomb purged and pressurized with nitrogen to at least about 500 psi. The bomb was rocked and heated through a desired temperature heating sequence which comprised, unless otherwise indicated, heating for about 1 hour at about 150° C., followed immediately by heating for 1 hour each at about 175° C., 200° C., and 225° C. (Examples containing alkaline earth catalysts were heated for 1 hour at about 100° C. and then for 1 hour at each of about 125° C., 150° C., 175° C., 200° and 225°.) After the heating sequence was complete, the rocker bomb was cooled to ambient temperature and the rocker bomb was vented and opened. The mini-bombs were immediately cooled in dry ice and finally in liquid nitrogen prior to opening. The sealed glass NMR tubes were removed from the mini-bombs and opened while cold. The solutions in the NMR tubes were transferred to vials and analyzed by gas chromatography (Hewlett Packard Model 5840A) using a six foot ⅛ inch TENAX-GC (trademark of Enka N.V., The Netherlands) column with a flame ionization detector sensitive to about 0.2 micrograms of crown ether present in a 0.2 microliter sample. Quantification was obtained by use of an internal standard (naphthalene). (Because of a retention time coincidence, relative amounts of ethylene carbonate and diethylene glycol were determined on a 12 foot ⅛ inch 20 percent OV-101 on CHROMOSORB-WHP (trademark of Johns Manville) column.)

The following examples are offered as illustrative of the present invention and are not to be construed as unduly limiting.

EXAMPLES 1-25

In accordance with these examples a number of ionic catalysts of cesium produced crown ethers when employed in admixture with acetone and ethylene carbonate as shown in Table I.

TABLE I

| EXAMPLE | IONIC CATALYST | CROWN ETHER[1] FORMED |
| --- | --- | --- |
| 1 | NaCl | + |
| 2 | NaBr | + |
| 3 | NaI | + |
| 4 | KCl | + |
| 5 | KBr | + |

TABLE I-continued

| EXAMPLE | IONIC CATALYST | CROWN ETHER[1] FORMED |
| --- | --- | --- |
| 6 | KI | + |
| 7 | RbCl | + |
| 8 | RbBr | + |
| 9 | RbI | + |
| 10 | CsCl | + |
| 11 | CsBr | + |
| 12 | CsI | + |
| 13 | CsNO$_3$ | + |
| 14 | CsOTs[2] | + |
| 15 | Cs$_2$SO$_4$ | + |
| 16 | CsBF$_4$ | + |
| 17 | CsBO$_4$ | + |
| 18 | Cs$_2$B$_{10}$H$_{10}$ | + |
| 19 | CsAsF$_6$ | + |
| 20 | Cs$_2$CrO$_4$ | + |
| 21 | CsSCN | + |
| 22 | CsOH | + |
| 23 | CsCN | + |
| 24 | CsF | + |
| 25 | Cs$_3$PO$_4$ | + |

[1] + indicates that crown ether was detected.
− indicates that crown ether was not detected.
[2] OTs indicates p-toluenesulfonate

EXAMPLES 26-37

In accordance with these examples 18-Crown-6 and 15-Crown-5 were produced with acetone as the solvent for ionic salts of cesium as shown in Table II:

TABLE II

| Example | Ionic Salt | Solvent | EC/Solvent[2] | Temperature[1] | Selectivities[3] | Cyclic Polyether Formed |
| --- | --- | --- | --- | --- | --- | --- |
| 26 | CsCl | Acetone | 1/1 | A | 13% <1% | 15-crown-5, 18-crown-6 |
| 27 | CsCl | Acetone | 2/1 | A | 10% 4% | 15-crown-5, 18-crown-6 |
| 28 | CsCl | Acetone | 1/1 | B | 5% | 15-crown-5 |
| 29 | CsCl | Acetone | 1/1 | C | 5% | 15-crown-5 |
| 30 | CsCl | Acetone | 1/1 | D | 8% 1% | 15-crown-5, 18-crown-6 |
| 31 | CsCl | Aceotne | 2/1 | D* | 15% <1% | 15-crown-5, 18-crown-6 |
| 32 | CsCl | Acetone | 1/1 | E | 9% 1% | 15-crown-5, 18-crown-6 |
| 33 | CsCl· | Acetone | 2/1 | E | 7% <1% | 15-crown-5, 18-crown-6 |
| 34 | CsCl | Acetone | 4/1 | E | — | — |
| 35 | CsBr | Acetone | 1/1 | N | 6% | 15-crown-5 |
| 36 | CsCl | Acetone | 1/2 | F | 11% | 15-crown-5 |
| 37 | CsCl | Acetone | 1/1 | N | 14% | 15-crown-5 |

[1] N: normal sequence, i.e., 1 hour each at 150, 175, 200, 225° C.
A: N + 15 hr. at 225° C.;
B: 60 hr. at 150° C.;
C: 10 hr. at 175° C.;
D: 10 hr. at 195° C.;
E: 4 hr. at 225° C.;
F: N + 4 hr. at 225° C.
[2] ratio by weight of ethylene carbonate (EC) to solvent
[3] Selectivities are the percentage of reacted carbonate which was converted to cyclic polyether.

EXAMPLES 38-77

In accordance with the examples, a number of solvents were evaluated for their ability to act as the solvent in the process of this invention by evaluating the solvent in a reaction system comprising CsCl, ethylene carbonate and the solvent such that the ethylene carbonate to solvent ratio is as shown in Table III. Examples 40-52 and 55 are comparative examples.

TABLE III

| Example | Solvent | EC:Solvent[2] | 15-Crown-5 or 18-Crown-6 Detected |
|---|---|---|---|
| 38 | acetone | 1/1 | + |
| 39 | acetonitrile | 1/1 | + |
| 40 | sulfolane | 0.6/1[3] | — |
| 41 | tetrahydrofuran | 1/1 | — |
| 42 | 15-crown-5 | 1/1 | — |
| 43 | 18-crown-6 | 1.0/0.12[3] | — |
| 44 | cyclopentanone | 1/4 | — |
| 45 | cyclohexanone | 1/4 | — |
| 46 | tetraglyme | 1/2 | — |
| 47 | pyridine | 1/1 | — |
| 48 | 1-methyl-2-pyrrolidinone | 2/1 | — |
| 49 | 1-3-dimethyl-2-imidazolidinone | 1/1 | — |
| 50 | tri-n-propylphosphine oxide | 2/1 | — |
| 51 | triphenylphosphine oxide | 2/1 | — |
| 52 | acetophenone | 1/1 | — |
| 53 | 2,4-pentanedione | 1/1 | + |
| 54 | dimedone | 2/1 | + |
| 55 | benzonitrile | 1/1 | — |
| 56 | mesityl oxide | 2/1 | + |
| 57 | butanone | 2/1 | + |
| 58 | 2-pentanone | 2/1 | + |
| 59 | 3-pentanone | 2/1 | + |
| 60 | 1,3-diphenyl-2-propanone | 1/1 | + |
| 61 | 1,2-diphenyl-2-propanone | 2/1 | + |
| 62[6] | butyrolactone | 2/1 | + |
| 63[6] | butyrolactone | 4/1 | + |
| 64[6] | benzyl cyanide | 1/1 | +[4] |
| 65[6] | diphenylacetonitrile | 2/1 | +[5] |
| 66[6] | n-butyronitrile | 1/1 | +[5] |
| 67[6] | n-butyronitrile | 2/1 | +[5] |
| 68[6] | n-butyronitrile | 4/1 | +[5] |
| 69[6] | isophorone | 2/1 | + |
| 70[6] | isophorone | 4/1 | + |
| 71[6] | dimethylmalonate | 2/1 | + |
| 72[6] | dimethylmalonate | 4/1 | + |
| 73 | diethylmalonate | 2/1 | + |
| 74[6] | 2-octanone | 2/1 | + |
| 75 | 2-heptanone | 2/1 | + |
| 76 | cycloheptanone | 2/1 | +[7] |
| 77 | 2-heptanone | 2/1 | +[7] |

[1] + = 15-Crown-5 or 18-Crown-6 detected.
— = no 15-Crown-5 or 18-Crown-6 detected.
[2] ratio by weight of ethylene carbonate (EC) to solvent unless otherwise indicated.
[3] ratio based on volume of ethylene carbonate (EC) to the volume of solvent.
[4] 12-Crown-4, 15-Crown-5 and 21-Crown-7 detected
[5] 18-Crown-6 and 21-Crown-7 detected
[6] heated at 200° C. for about 10 hours.
[7] a mixture of crown ethers was observed.

EXAMPLE 78

According to this invention, 22 grams of ethylene carbonate, 11 grams of 2-decanone and 0.565 grams of CsCl were placed in a 100 ml round-bottomed flask which was fitted with a thermometer, distillation head and a cold trap. The flask was heated in an oil bath (with magnetic stirring) at about 150° C. to about 175° C. for about 8 hours. Analysis of the reaction mixture by gas chromatography showed that 15-Crown-5 and 18-Crown-6 were formed.

COMPARATIVE EXAMPLES 79–106

To test the effect on formation of cyclic polyethers when solvents not of the invention are employed as solvents in admixture with ionic catalysts and ethylene carbonate comparative examples 79–106 were carried out. The formation of cyclic polyether was not observed as is shown in Table IV:

TABLE IV[1,2]

| Example | Catalyst | Solvent[3] | | | |
|---|---|---|---|---|---|
| | | None | Sulfolane | Butyrolactone | Acetonitrile |
| 79 | NaCl | 202° C. | 205° C. | — | 75° C. |
| 80 | NaBr | 178° C. | 204° C. | — | 75° C. |
| 81 | NaI | 151° C. | 173° C. | — | — |
| 82 | KCl | 195° C. | 227° C. | 206° C. | — |
| 83 | KBr | 195° C. | 227° C. | 206° C. | — |
| 84 | KI | 173° C. | 227° C. 230° C. | 206° C. | — |
| 85 | RbCl | 185° C. | 190° C. 196° C. | — | — |
| 86 | RbBr | 189° C. | — | — | — |
| 87 | RbI | 177° C. | — | — | — |
| 88 | CsCl | 185° C. | 202° C. | 195° C. | 75° C. |
| 89 | CsBr | 200° C. | 202° C. | 195° C. | 75° C. |
| 90 | CsI | 185° C. | 202° C. | 195° C. | 75° C. |
| 91 | CaCl$_2$ | 152° C. | — | — | — |
| 92 | CaBr$_2$ | 152° C. | — | — | — |
| 93 | BaCl$_2$ | 226° C. | — | — | — |
| 94 | BaBr$_2$ | 187° C. | — | — | — |
| 95 | BaI$_2$ | 196° C. | — | — | — |
| 96 | AgCl | 173° C. | 206° C. | 206° C. | — |
| 97 | AgBr | 173° C. | 230° C. | — | — |
| 98 | AgI | 202° C. | 230° C. | — | — |
| 99 | TlCl | 196° C. | 231° C. | — | — |
| 100 | TlI | 231° C. | — | — | — |
| 101 | CdCl$_2$ | 226° C. | — | — | — |
| 102 | CdBr$_2$ | 231° C. | — | — | — |
| 103 | CdI$_2$ | 231° C. | — | — | — |
| 104 | PbCl$_2$ | 196° C. | — | — | — |
| 105 | PbBr$_2$ | 196° C. | — | — | — |
| 106 | — | 225° C. | — | — | — |

[1] No cyclic polyether formed in Examples 79–106.
[2] The temperature indicated for each solvent and ionic catalyst corresponds to the highest temperature reached in carrying out the example.
[3] — indicates that no example was run for this particular combination of catalyst and solvent.

COMPARATIVE EXAMPLES 107–127

To demonstrate the effect of ionic catalysts in producing cyclic polyethers when placed in admixture with ethylene carbonate in the absence of a solvent the ionic catalysts of Table V were tested according to the experimental procedure.

No cyclic polyether was observed in the reaction mixtures of examples 107–127.

TABLE V

| Example | Ionic Catalyst |
|---|---|
| 107 | NaCl |
| 108 | KCl |
| 109 | KBr |
| 110 | KI |
| 111 | RbCl |
| 112 | CsCl |
| 113 | CsBr |
| 114 | CsI |
| 115 | Cs$_3$PO$_4$ |
| 116 | AgCl |
| 117 | CaCl$_2$ |
| 118 | CaBr$_2$ |
| 119 | CaI$_2$ |
| 120 | SrCl$_2$ |
| 121 | SrBr$_2$ |
| 122 | SrI$_2$ |
| 123 | BaCl$_2$ |
| 124 | BaBr$_2$ |
| 125 | BaI$_2$ |
| 126 | BF$_3$Et$_2$O |
| 127[1] | — |

[1] Example 127 is pure ethylene carbonate.

EXAMPLE 128

To inquire into the nature of the present process the following experiments were conducted:

(a) To determine whether ethylene carbonate is serving simply as an in situ source of ethylene oxide, which may then be the actual substrate, the process was carried out according to the experimental procedure except that ethylene oxide was employed instead of ethylene carbonate and various halide salts were tested using acetone and acetonitrile as co-solvents. (CsCl, RbCl, KCl, CsBr and CsI). Only CsI produced crown ethers which is consistent with applicants' copending U.S. Pat. No. 248,532 and indicative of the uniqueness of ethylene carbonate as the substrate of this process;

(b) Since glycols are by-products of the reaction and could conceivably cyclize, the process was carried out according to the experimental procedure except that the ethylene carbonate was replaced by CARBOWAX 200 (TM) (a mixture of glycols having from 3 to 8 carbon atoms) using CsCl and CsCl/$CO_2$ as the catalysts. No crown ethers were found. This experiment, like those with ethylene oxide, is indicative, but not definitive, since the ethylene oxide and CARBOWAX were not subjected to the specific conditions of the reaction whereby ethylene carbonate is converted to crown ethers.

(c) The process was carried out according to the experimental procedure using an acetone-$d_6$ co-solvent to determine the activity, if any, of the co-solvent acetone in the process. The chemical ionization mass spectrum of formed 15-crown-5 indicated no deuterium present therein; and (d) The process was carried out according to the experimental procedure to determine the effect of water on the process. Three mmoles of water increased the amount of ethylene glycol formed and reduced the amount of 15-crown-5 formed.

What is claimed is:

1. A process for the preparation of cyclic polyethers of the formula:

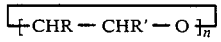

from cyclic alkylene carbonates of the formula:

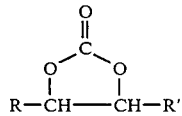

wherein R and R' are each selected from the group consisting of hydrogen and alkyl having from 1 to 10 carbon atoms; n is an integer having a value of at least 3 wherein said process comprises providing in admixture at a temperature from about 100° C. to about 300° C. said cyclic alkylene carbonate, a solvent wherein said solvent contains at least one moiety from the group consisting of carbonyl, nitrile and mixtures thereof, and a catalyst selected from the group consisting of salts of Group IA, IIA, IB or IIB metals such that said cyclic polyether is produced.

2. Process according to claim 1 wherein R and R' are hydrogen.

3. Process according to claim 1 wherein n equals 5 and the solvent is acetone.

4. Process according to claim 1 wherein n equals 6 and the solvent is acetone.

5. Process according to claim 1 wherein the catalyst is a salt of a Group IA metal.

6. Process according to claim 5 wherein the salt is a halide.

7. Process according to claims 6 wherein said catalyst is present at a concentration of from 0.01 to about 10 molar.

8. Process according to claim 1 wherein the process is carried out at superatmospheric pressure.

9. Process according to claim 1 wherein the ratio by weight of solvent to cyclic alkylene carbonate is from about 5:95 to 95:5.

10. Process according to claim 9 wherein said ratio of solvent to cyclic alkylene carbonate is from about 1:10 to about 10:1.

11. Process according to claim 10 wherein said ratio of solvent to cyclic alkylene carbonate is from about 1:4 to about 4:1.

12. A process for preparing a cyclic polyether of the formula:

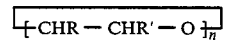

from cyclic alkylene carbonates of the formula:

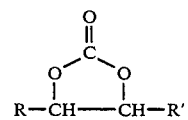

wherein R and R' are each selected from the group consisting of hydrogen and alkyl having from 1 to 10 carbon atoms; and n is 5 or 6, wherein said process comprises providing in admixture at a temperature from about 100° C. to about 300° C. said cylic alkylene carbonate, a solvent containing at least one moiety from the group consisting of carbonyl and nitrile, and a cesium halide catalyst such that said cylic polyether is formed.

13. The process of claim 12 wherein the cesium halide catalyst comprises at least one selected from the group consisting of cesium chloride and cesium bromide and is present at a concentration of from 0.01 to about 10 molar.

14. The process of claim 13 wherein R and R' are hydrogen.

15. The process of claim 14 wherein the temperature is from about 150° C. to about 225° C.

16. The process of claim 14 wherein the solvent comprises acetone, and the ratio by weight of the solvent to the cyclic alkylene carbonate is from about 5:95 to about 95:5.

* * * * *